(12) United States Patent
Hobbs et al.

(10) Patent No.: US 7,563,929 B2
(45) Date of Patent: *Jul. 21, 2009

(54) ALKYLATION OF N'-PHENYL-N-ALKYLPHENYLENEDIAMINES IN IONIC LIQUID AND N'-PHENYL-N-ALKYL(ALKYLPHENYLENE) DIAMINES PRODUCED THEREBY

(75) Inventors: Steven J. Hobbs, Wolcott, CT (US); Joseph F. Stieber, Prospect, CT (US)

(73) Assignee: Chemtura Corporation, Middlebury, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/103,835

(22) Filed: Apr. 16, 2008

(65) Prior Publication Data
US 2008/0234517 A1 Sep. 25, 2008

Related U.S. Application Data

(63) Continuation of application No. 11/304,829, filed on Dec. 14, 2005, now Pat. No. 7,390,928.

(51) Int. Cl.
*C07C 209/68* (2006.01)
(52) U.S. Cl. .................................... 564/309
(58) Field of Classification Search ................ None
See application file for complete search history.

(56) References Cited

U.S. PATENT DOCUMENTS

| | | | |
|---|---|---|---|
| 2,943,112 A | 6/1960 | Popoff et al. | |
| 4,824,601 A | 4/1989 | Franklin | |
| 4,973,759 A | 11/1990 | Klein et al. | |
| 5,214,211 A | 5/1993 | Kurek et al. | |
| 5,232,614 A | 8/1993 | Colclough et al. | |
| 5,672,752 A | 9/1997 | Lai et al. | |
| 5,734,084 A | 3/1998 | Zhu | |
| 5,750,787 A | 5/1998 | Lai et al. | |
| 5,994,602 A * | 11/1999 | Abdul-Sada et al. | 585/457 |
| 6,315,925 B1 | 11/2001 | Aebli et al. | |
| 7,145,038 B1 | 12/2006 | Hobbs | |

FOREIGN PATENT DOCUMENTS

| | | |
|---|---|---|
| EP | 0 807 620 | 11/1997 |
| GB | 2 325 929 | 12/1998 |
| JP | 55 053249 | 4/1980 |

OTHER PUBLICATIONS

Doklady Akademii Nauk SSSR (1984), 274(2), p. 335-8 (CAPLUS abstract).*
Parkinson, "Ionic Liquids Make an Environment Splash," 100 Chemical Engineering Progress; 7 (Sep. 2004).
Venuto et al., "Organic Reactions Catalyzed by Crystalline Aluminosilicates" 4 Journal of Catalysis 81-98 (1966).
Holbrey, "Industrial Applications of Ionic Liquids," Chemistry Today 35 (Jun. 2004).
Wilkes, "Friedel-Crafts Reactions of Chloroaluminate Molten Salts," Molten Salt Chemistry: An Introduction and Selected Applications 405 (Mamantov and Marassi Eds. 1987).
Nelson, "Are Ionic Liquids Green Solvents?" 818 ACS Symposium Series 30-41, (American Chemical Society 2002).
Davis et al., "Synthesis and Purification of Ionic Liquids," Ionic Liquids in Synthesis 41 (Wasserschied & Welton Eds. 2003).
Anthony et al., "Physicochemical Properties of Ionic Liquids," Ionic Liquids i Synthesis 41 (Wasserschied & Welton Eds. 2003).
Earle et al., "Organic Synthesis," Ionic Liquids in Synthesis 174 (Wasserschied & Welton Eds. 2003).
Drake et al., "Structural Effects on the Physical Properties of Ionic Liquids," Air Force Research Laboratory Report No. AFRL-PF-ED-VG-2003-122 (May 2003).
"BASILTM—First Commercial Process Using Ionic Liquids" Chemicals Research and Engineering http://www.corporate.basf.com/en/innovationen/labors/chemikalien.
Boswell, "Technology Watch: Ionic Liquids Offer New Solutions" Chemical Market Reporter FR14-16 (Jan. 2004).
Fremantle, "Designer Liquids in Polymer Systems" Chemical and Engineering New 26-29 (May 2004).

* cited by examiner

*Primary Examiner*—Brian J Davis
(74) *Attorney, Agent, or Firm*—Jaimes Sher

(57) ABSTRACT

A process for alkylation of a N'-phenyl-N-alkyl-p-phenylenediamine of specified formula in an ionic liquid unexpectedly produces a N'-phenyl-N-alkyl(alkylphenylene)diamine of a second specified formula. The use of an inorganic liquid permits convenient separation of the alkylated reaction product from the reaction mixture.

19 Claims, No Drawings

ALKYLATION OF N'-PHENYL-N-ALKYLPHENYLENEDIAMINES IN IONIC LIQUID AND N'-PHENYL-N-ALKYL(ALKYLPHENYLENE) DIAMINES PRODUCED THEREBY

This application is a continuation of U.S. application Ser. No. 11/304,829 filed Dec. 14, 2005, now U.S. Pat. No. 7,390,928, which is incorporated herein by reference in its entirety.

BACKGROUND OF THE INVENTION

N'-phenyl-N-alkylphenylenediamines have utility as antioxidants for lubricant oils, rubber compositions and antiozonants. U.S. Pat. No. 5,232,614 discloses the use of N,N'-dialkylsubstituted p-phenylenediamines as antioxidants in lubricating oils.

The Friedel-Crafts alkylation of N'-phenyl-N-phenylenediamine compounds using alpha-olefins and a Lewis acid catalyst such as aluminum chloride provides little or no yield of alkylated product. Instead, an aluminum alkyl catalyst and high pressure may be used to alkylate N'-phenyl-N-phenylenediamines.

The use of aluminum alkyls to alkylate a N'-phenyl-N-alkylphenylenediamine has at least two disadvantages: the compounds are not recyclable, and they may spontaneously ignite in air. Moreover, the reaction typically alkylates the non-substituted phenyl ring. Thus, for example, the use of triethylaluminum chloride, heat and pressure to alkylate N'-phenyl-N-isohexylphenylenediamine with 1-decene produces predominantly N'-2-methylnonylphenyl-N-isohexylphenylenediamine.

An ionic liquid consists of inorganic and/or organic cations and anions, and typically has a very low vapor pressure, a wide liquid temperature range, and is non-flammable. Ionic liquids can act as a catalyst and/or solvent, and have been studied for utility as solvents, electrolytes, in separations and in fluid applications such as lubricants. See Holbrey, "Industrial Applications of Ionic Liquids," *Chemistry Today* 35 (June 2004); Parkinson, "Ionic Liquids Make an Environmental Splash," 100 *Chemical Engineering Progress* 7 (September 2004); and Drake et al., "Structural Effects on the Physical Properties of Ionic Liquids," *Air Force Research Laboratory Report No.* AFRL-PR-ED-VG-2003-12 (May 2003).

The use of ionic liquids in Friedel-Crafts alkylation has been discussed in Wilkes, Friedel-Crafts Reactions in Chloroaluminate Molten Salts," *Molten Salt Chemistry: An Introduction and Selected Applications* 405 (Mamantov and Marassi Eds. 1987) and Earle et al, "Organic Synthesis," *Ionic Liquids in Synthesis* 174 (Wasserschied & Welton Eds. 2003). However, neither study is directed to an alkylation reaction which permits further substitution of the phenylene ring of an N'-phenyl-N-alkylphenylenediamine compound.

An object of the invention is to provide a synthesis which permits alkylation of the phenylene ring of an N'-phenyl-N-phenylenediamine compound.

A feature of the invention is the use of an ionic liquid as a solvent and catalyst for the alkylation reaction.

An advantage of the invention is that use of an ionic liquid typically permits convenient separation of N'-phenyl-N-alkyl(alkylphenylene)diamine from the reaction mixture.

BRIEF SUMMARY OF THE INVENTION

In one aspect, the present invention relates to a process for alkylating a N'-phenyl-N-alkylphenylenediamine, comprising reacting a N'-phenyl-N-alkylphenylenediamine of Formula I

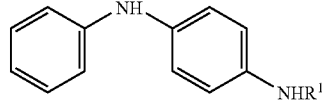

Formula I wherein $R^1$ is an alkyl group or an arylalkyl group, with an alkylating agent in the presence of an ionic liquid comprising a Lewis acid and a quaternary cation, to produce a N'-phenyl-N-alkyl(alkylphenylene)diamine of Formula II

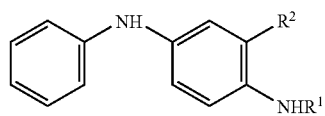

Formula II wherein $R^1$ is as defined above, and
$R^2$ is a substituted or unsubstituted linear, branched or cyclic alkyl group or an alkylaryl group.

In another aspect, the present invention relates to a N'-phenyl-N-alkyl(alkylphenylene)diamine of Formula II

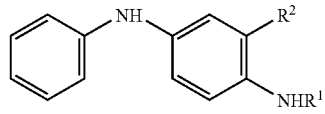

Formula II wherein $R^1$ is an alkyl group or an arylalkyl group; and
$R^2$ is a substituted or unsubstituted linear, branched or cyclic alkyl group or an alkylaryl group, prepared by a process comprising:

reacting a N'-phenyl-N-alkylphenylenediamine of Formula I

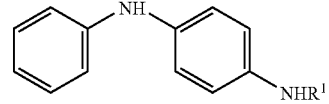

Formula I wherein $R^1$ is an alkyl group or an arylalkyl group, with an alkylating agent in the presence of an ionic liquid comprising a Lewis acid and a quaternary cation.

In yet another aspect, the present invention relates to a lubricant composition comprising a lubricating oil and a N'-phenyl-N-alkyl(alkylphenylene)diamine of Formula II

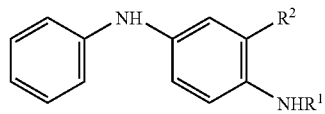

Formula II wherein $R^1$ is an alkyl group or an arylalkyl group; and $R^2$ is a substituted or unsubstituted linear, branched or cyclic alkyl group or an alkylaryl group.

DETAILED DESCRIPTION OF THE PREFERRED EMBODIMENTS

As summarized above, the present invention relates to the Friedel-Crafts alkylation of a N'-phenyl-N-alkylphenylenediamine in the presence of an inorganic liquid.

The alkylating agent may be a substituted or unsubstituted linear, branched or cyclic olefin or an arylalkene. Suitable linear olefins include 1-hexene, 1-nonene, 1-decene and 1-dodecene. Suitable cyclic olefins include cyclohexene, cyclopentene and cyclooctene. Suitable branched olefins include propylene trimer (nonenes), propylene tetramer (dodecenes), propylene pentamer and diisobutylene. Suitable arylalkylenes include styrene, methyl styrene, 3-phenylpropene and 2-phenyl-2-butene.

The ionic liquid may be composed entirely of anions and cations, and may conveniently be prepared by mixing together a Lewis acid and an alkyl quaternary metal salt, preferably under heat.

The Lewis acid may be a metal halide, an alkyl halide, an alkylaryl, or an alkyl sulfonate ester. Suitable Lewis acid metal halides include aluminum chloride, aluminum bromide, indium trichloride, gallium trichloride, niobium pentachloride, tantalum pentachloride, titanium tetrachloride, boron trifluoride, boron trifluoride etherate, boron trichloride, ferric chloride, and zirconium chloride. Illustrative alkyl halides include methyl chloride, methyl bromide, methyl iodide, ethyl chloride, ethyl bromide, ethyl iodide, n-propyl chloride, n-propyl bromide, n-propyl iodide, isopropyl chloride, isopropyl bromide, isopropyl iodide, n-butyl chloride, n-butyl bromide, n-butyl iodide, isobutyl chloride, isobutyl bromide, isobutyl iodide, tert-butyl chloride, tert-butyl bromide, tert-butyl iodide, n-pentyl chloride, n-pentyl bromide, n-pentyl iodide, neopentyl bromide, neopentyl chloride, neopentyl iodide, octyl chloride, octyl bromide and octyl iodide. Illustrative alkylaryl halides include benzyl bromide, benzyl chloride, benzyl iodide, α-phenylethyl chloride, α-phenylethyl bromide, α-phenylethyl iodide, β-phenylethyl chloride, β-phenylethyl bromide and β-phenylethyl iodide. Suitable alkyl sulfonate esters include alkyl tosylates, alkyl mesylates and alkyl triflates.

The alkyl quaternary metal salt may be a quaternary ammonium salt, an alkylphosphonium salt, an alkylimidazolium salt, an alkyltriazolium salt and an alkylpyridinium salt. Suitable quaternary ammonium salts may be based on cations selected from the group consisting of benzyltrimethylammonium, butyltrimethylammmonium, methyltriethylammonium, ethyltrimethylammonium, tetra-n-butylammonium, n-hexyl-trimethylammonium, n-heptyl-trimethylammonium, n-octyl-trimethylammonium, n-hexyl-triethylammonium, n-heptyl-triethylammonium, n-octyl-triethylammonium, n-hexyl-tri-n-butylammonium, n-heptyl-tri-n-butylammonium, n-octyl-tri-n-butylammonium, tris-(n-propyl)-undecylammonium, tetra-n-pentylammonium, N-decyl-n-octyl-dimethylammonium and N-tetradecyl-triethylammonium.

Suitable alkylphosphonium salts may be based on cations selected from the group of benzyltrimethylphosphonium, butyltrimethylphosphonium, methyltriethylphosphonium, ethyltrimethylphosphonium, tetra-n-butylphosphonium, n-hexyl-trimethylphosphonium, n-heptyl-trimethylphosphonium, n-octyl-trimethylphosphonium, n-hexyl-triethylphosphonium, n-heptyl-triethylphosphonium, n-octyl-triethylphosphonium, n-hexyl-tri-n-butylphosphonium, n-heptyl-tri-n-butylphosphonium, n-octyl-tri-n-butylphosphonium, tris-(n-propyl)-undecylphosphonium, tetra-n-pentylphosphonium, N-decyl-n-octyl-dimethylphosphonium and N-tetradecyl-triethylphosphonium.

Suitable imidazolium salts may be based on cations selected from the group consisting of 1-methyl-3-methylimidazolium, 1-ethyl-3-methyl-imidazolium, 1-butyl-3-methylimidazolium, 1-dodecyl-5-methylimidazolium, 1-(2,2,2-trifluoroethyl)-3-methylimidazolium, 1-(ethoxymethyl)-3-methylimidazolium, 3-ethyl-1-ethylimidazolium, 3-ethyl-l-butyl-imidazolium, 1-ethyl-2,3-dimethyl-imidazolium, 1,2-diethyl-3-methylimidazolium, 1-ethyl-3,5-dimethylimidazolium and 1,3-diethyl-5-methylimidazolium.

Suitable alkyltriazonium salts may be based on cations selected from the group consisting of 1-(3',3',3'-trifluoro-n-propyl)-3-n-butyl-1,2,4-triazolium, 1-(2'-fluoroethyl)-3-n-heptyl-1,2,4-triazolium, 1-(2'-fluoroethyl)-3-n-decyl-1,2,4-triazolium, 1-(1H,1H,2H,2H-perfluoro-n-hexyl)-3-n-butyl-1,2,4-triazolium, 1-n-propyl-4-amino-1,2,4-triazolium, 1-n-butyl-4-amino-1,2,4-triazolium and 1-n-hexyl-4-amino-1,2,4-triazolium.

In a preferred embodiment, the ionic liquid is formed in situ prior to addition of the alkylating agent. The Lewis acid, alkyl quaternary metal salt and N'-phenyl-N-alkylphenylenediamine may be added to a suitable reaction vessel, preferably under a dry, inert atmosphere and with heating to a temperature up to 200° C., and stirred, for example at 200 to 300 rpm, until an ionic liquid phase and an organic phase are formed. The inert atmosphere serves to protect the ionic liquid from oxidation, and is preferably selected from the group consisting of argon, helium and nitrogen. The inert atmosphere should also be dry to avoid decomposition of the ionic liquid.

The alkylating agent may be added to the reaction vessel once the two phases have been formed, either all at once or by multiple partial additions.

The alkylation reaction may preferably be performed at a temperature of from 80 to 200° C. over a time period of from 1 to 24 hours.

The alkylation reaction produces a mixture of mono, di and tri-alkylated N'-phenyl-N-alkylphenylenediamines. The reaction products may be separated from the reactants by conventional separation techniques and apparatus, such as a separatory funnel well known to one of ordinary skill in the art. Similarly, the isolated reaction mixture may be separated into its component compounds using conventional separation techniques and apparatus well known to those of ordinary skill in the art, such as, for example, high pressure liquid chromatography.

The Friedel-Crafts alkylation of N'-phenyl-N-alkylphenylene-diamine in an ionic liquid as described above unexpectedly produces a N'-phenyl-N-alkyl(alkylphenylene)diamine of formula II:

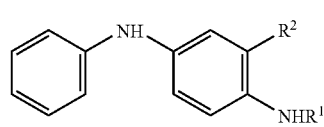

Formula II wherein $R^1$ is an alkyl group or an arylalkyl group, preferably having from 1 to 30 carbon atoms; and $R^2$ is a substituted or unsubstituted linear, branched or cyclic alkyl group or an alkylaryl group, preferably having from 1 to 30 carbon atoms.

Preferred N'-phenyl-N-alkyl(alkylphenylene)diamine compounds include those in which $R^1$ and $R^2$ are both n-2-decyl, where $R^1$ is 2-isohexyl and $R^2$ is n-2-decyl, and where at least one of $R^1$ and $R^2$ is an arylalkyl group.

The N'-phenyl-N-alkyl(alkylphenylene)diamine compounds prepared by the process of the present invention are believed suitable for use as antioxidants in lubricant compositions such as those described in U.S. Pat. No. 5,232,614, the disclosure of which is hereby incorporated by reference in its entirety. Typically, the lubricant composition will include at least a lubricating oil and at least one N'-phenyl-N-alkyl (alkylphenylene)diamine as an antioxidant. However, the composition may also include one or more members of the group consisting of a dispersant, a detergent, an antiwear additive, a pour point depressant, a corrosion inhibitor and a friction modifier.

The lubricating oil may be a hydrocarbon oil derived from petroleum or a long chain hydrocarbon substituted with an alpha-or beta-unsaturated carboxylic acid. The detergent, when present, may be an alkali metal sulfonate, an alkaline earth metal sulfonate or a metal salt of a sulfur-containing alkylphenol compound.

The antiwear additive, when present, may be an organic sulfide, a polysulfide, an ester of beta-thiodipropionic acid, a phosphorus ester or a dihydrocarbyl dithiophosphate metal salt.

The corrosion inhibitor, when present, may be a benzotriazole derivative, a thiadiazole compound, a mercaptobenzothioazole compound in the form of an amine salt, a sulfonamide, a thiosulfonamide, a condensate of mercaptobenzothiazole with an amine and formaldehyde, a dialkylphosphite, a trialkylphosphite or a triarylphosphite.

The friction modifier, when present, may be a glyceryl monoester of a higher fatty acid or an oxazoline compound.

The inventors currently believe the ionic liquid may be recycled for use in subsequent alkylations by simple phase separation in which the hydrocarbon-soluble reaction product is decanted, and thus separated from, the denser ionic liquid phase.

The ionic liquid may then be used to catalyze another alkylation reaction by itself, or in combination with fresh catalyst.

EXAMPLE

The following Example illustrates the practice and advantages of the invention in greater detail with respect to an individual species thereof. The details of the example are illustrative only, and are not to be used to constrict the scope of the claims.

Example 1

A 1-L, 4-necked round bottomed flask equipped with a mantle, temperature controller, thermocouple, and pressure equilibrated dropping funnel was charged under nitrogen positive pressure with solid N'-phenyl-N-2-isohexyl-p-phenylenediamine (53.38 g, 0.1989 mole) commercially available as Flexzone 7P from Chemtura Corp., aluminum chloride (13.37 g, 0.100 mole, 50.4 mole % relative to N'-phenyl-N-2-isohexyl-p-phenylenediamine) and tetra-n-butylammonium bromide (21.34 g, 0.0661 mole, 33.3 mole % relative to N'-phenyl-N-2-isohexyl-p-phenylenediamine). Stirring was started at ca. 200-300 rpm and the mixture warmed to 160° C.

When the dark brown-black reaction mixture had reached 160° C., 94% 1-decene (97.64 g, 0.696 mole, 3.5 equiv. relative to N'-phenyl-N-2-isohexyl-p-phenylenediamine) was added over 2 hr. The reaction mixture was brought to 170° C. upon completion of the addition and maintained at this temperature for 25 hr.

The reaction product was then allowed to cool down to ambient temperature and was diluted with 300 mL n-heptane. The dark brown-black reaction mixture separated into a lower solid phase and an upper liquid phase, which was decanted into a 2-L separatory funnel, washed with 2× 500 mL water and then 400 mL water-100 mL conc. aqueous ammonia, and then dried over anhydrous sodium sulfate. The solid phase at the bottom of the flask weighed 50.74 g.

The drying agent was removed from the product by suction filtration through a 9.0 cm diameter disk of 934 AH glass fiber paper. The dark filtrate was then condensed in vacuo (rotary evaporator, 95° C. water bath, <5 mm final vacuum) to obtain 49.49 g of a dark brown-black oil.

GC analysis of the oil indicated that it was a mixture of (area %) 17.1% unreacted N'-phenyl-N-2-isohexyl-p-phenylenediamine, 71.8% mono-decylated N'-phenyl-N-2-isohexyl-p-phenylenediamine and 7.5% multi-decylated N'-phenyl-N-2-isohexyl-p-phenylenediamine. The monodecylated product was a mixture of two isomers: 8.2% and 63.6%. The major isomer was isolated by column chromatography.

The major isomer was identified as N'-phenyl-N-2-isohexyl-[2-(2-isodecyl)-p-phenylene)]diamine (GRFE) by its GC retention time, IR spectra and NMR spectra, which were consistent with the GC retention time, IR spectra and NMR spectra of an authentic GRFE sample prepared using a different synthesis route, i.e., from 1-decene using diethyl aluminum chloride as a catalyst, heat and high pressure.

The inventors currently believe the ionic liquid may be recycled for use in subsequent alkylations by simple phase separation in which the hydrocarbon-soluble reaction product (s) is/are decanted, and thus separated from, the denser ionic liquid phase. The ionic liquid may then be used to catalyze another alkylation reaction by itself, or in combination with fresh catalyst.

We claim:

1. A process for alkylating a N'-phenyl-N-alkylphenylenediamine comprising reacting a N'-phenyl-N-alkylphenylenediamine of Formula I

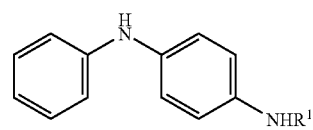

Formula I wherein $R^1$ is an alkyl group or an arylalkyl group,
with an alkylating agent in the presence of an ionic liquid comprising a Lewis acid and a quatemary cation, to produce a N'-phenyl-N-alkyl(alkylphenylene)diamine of the Formula II

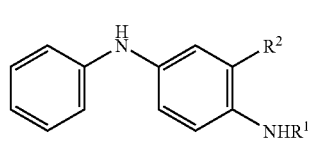

Formula II wherein $R^1$ is as defined above, and

R² is a substituted or unsubstituted linear, branched or cyclic alkyl group or an alkylaryl group.

2. The process of claim 1, wherein said alkylating agent is a substituted or unsubstituted linear, branched or cyclic olefin or an arylalkene.

3. The process of claim 2, wherein said olefin is a linear olefin selected from the group consisting of 1-hexene, 1-nonene, 1 decene and 1-dodecene.

4. The process of claim 2, where said olefin is a cylcic olefin selected from the group consisting of cyclohexene, cyclopentene and cyclooctane.

5. The process of claim 2, wherein said olefin is a branched olefin selected from the group consisting of propylene trimer, propylene tetramer, propylene pentamer and diisobutylene.

6. The process of claim 2, wherein said olefin is an arylalkene selected from the group consisting of styrene, methyl styrene, 3-phenylpropene and 2-phenyl-2-butene.

7. The process of claim 1, wherein said Lewis acid is a metal halide selected from the group consisting of aluminum chloride, aluminum bromide, indium trichloride, gallium trichloride, niobium pentachloride, tantalum pentachloride, titanium tetrachloride, boron trifluoride, boron trifluoride etherate, boron trichloride, ferric chloride, and zirconium chloride.

8. The process of claim 1, wherein said Lewis acid is an alkyl halide selected from the group consisting of methyl chloride, methyl bromide, methyl iodide, ethyl chloride, ethyl bromide, ethyl iodide, n-propyl chloride, n-propyl bromide, n-propyl iodide, isopropyl chloride, isopropyl bromide, isopropyl iodide, n-butyl chloride, n-butyl bromide, n-butyl iodide, isobutyl chloride, isobutyl bromide, isobutyl iodide, tert-butyl chloride, tert-butyl bromide, tert-butyl iodide, n-pentyl chloride, n-pentyl bromide, n-pentyl iodide, neopentyl bromide, neopentyl chloride, neopentyl iodide, octyl chloride, octyl bromide and octyl iodide.

9. The process of claim 1, wherein said Lewis acid is an alkylaryl halide selected from the group consisting of benzyl bromide, benzyl chloride, benzyl iodide, α-phenylethyl chloride, α-phenylethyl bromide, α-phenylethyl iodide, β-phenylethyl chloride, β-phenylethyl bromide, and β-phenylethyl iodide.

10. The process of claim 1, wherein said Lewis acid is an alkyl sulfonate ester.

11. The process of claim 1, wherein said quatemary cation is selected from a quatemary ammonium cation, an alkylphoshonium cation, an alkylimidazolium cation, an alkyltriazolium cation and an alkylpyridinium cation.

12. The process of claim 11, wherein said quatemary ammonium cation is a member selected from the group consisting of benzyltrimethylammonium, butyltrimethylammonium, methyltriethylammonium, ethyltrimethylammonium, tetra-n-butylammonium, n-hexyl-trimethylammonium, n-heptyl-trimethylammonium, n-octyl-trimethyammonium, n-hexyltriethyammonium, n-heptyl-triethylammonium, n-octyl-triethylammonium, n-hexyl-tri-n-butylammonium, n-heptyl-n-butylammonium, n-octyl-tri-n-butylammonium, tris-(N-propyl)-undecylammonium, tetra-n-pentylammonium, n-decyl-n-octyl-dimethylammonium and n-tetradecyl-triethyammonium.

13. The process of claim 11, wherein said alkylphosphonium cation is selected from the group of benzyltrimethylphosphoniom, butyltrimethylphosphoniom, methyltriethyiphosphoniom, ethyltrimethylphosphonium, tetra-n-butylphosphonium, n-hexyl-trimethylphosphonium, n-heptyl-trimethylphosphonium, n-octyl-trimethylphosphonium, n-hexyl-triethylphosphonium, n-heptyl-triethylphosphonium, n-octyl-triethylphosphonium, n-hexyl-tri-n-butylphosophonium, n-heptyl-tri-n-butylphosophonium, n-octyl-tri-n-butylphosophonium, tris-(n-propyl)-undecylphosphonium, tetra-n-pentylphosphonium, N-decyl-n-octyl-dimethylphosphonium and N-tetradecyl-triethylphopsphonium.

14. The process of claim 11, wherein said alkylimidaxolium cation is a member selected form the group consisting of 1-methyl-2-methylimidazolium, 1-ethyl-3-methyl-imidazolium, 1-butyl-3-methyl-imidazolium, 1-dodecyl-5-methylimidazolium, 1-(2,2,2-trifluoroethyl)-3-methylimidazolium, 1-(ethoxymethyl)-3-methylimidazolium, 3-ethyl-1-ethylimidazolium, 3-ethyl-1-butylimidazolium, 1-ethyl-2,3-dimethyl-imidazolium, 1,2-diethyl-3-methylimidazolium, 1-ethyl-3,5-dimethyl-imidazolium and 1,3-diethyl-5-methylimidazolium.

15. The process of claim 11, wherein said alkyltriazolium cation is a member selected from the group consisting of 1-(3',3',3'-trifluoro-n-propyl)-3-n-butyl-1,2,4-triazolium, 1-(2'-fluoroethyl)-3-n-heptyl-1,2,4-triazolium, 1-(2'-fluoroethyl)-3-n-3-decyl-1,2,4-trizolium, 1-(1H,1H,2H,2H-perfluoro-n-hexyl)-3-n-butyl-1,2,4-triazolium, 1-n-propyl-4-amino-1,2,4-triazolium, 1-n-butyl-4-amino-1,2,4-triazolium and 1-n-hexyl-4-amino-1,2,4-triazolium.

16. The process of claim 1, wherein said ionic liquid is formed in situ prior to addition of said alkylating agent.

17. The process of claim 1, performed at a temperature of from 80 to 200° C. over a time period of from 1 to 24 hours.

18. The process of claim 1, performed under an inert atmosphere selected from the group consisting of argon, helium and nitrogen.

19. The process of claim 1, performed with stirring at a stirring speed of from 200 to 300 rpm.

* * * * *